United States Patent [19]

Knauf et al.

[11] Patent Number: 5,530,194
[45] Date of Patent: Jun. 25, 1996

[54] SEQUENCES PREFERENTIALLY EXPRESSED IN EARLY SEED DEVELOPMENT AND METHODS RELATED THERETO

[75] Inventors: Vic C. Knauf, Winters; Jean C. Kridl, Davis; Donna E. Scherer, Sacramento, all of Calif.

[73] Assignee: Calgene, Inc., Davis, Calif.

[21] Appl. No.: 242,743

[22] Filed: Oct. 19, 1992

Related U.S. Application Data

[63] Continuation of Ser. No. 494,722, Mar. 16, 1990, abandoned.

[51] Int. Cl.$^6$ ............................. A01H 4/00; C12N 15/82
[52] U.S. Cl. ................... 800/205; 435/240.4; 435/320.1; 435/172.3; 800/255; 800/DIG. 16; 800/DIG. 69
[58] Field of Search ........................ 536/23.6; 435/320.1, 435/172.3; 800/205, DIG. 15, DIG. 16, 255, DIG. 69

[56] References Cited

U.S. PATENT DOCUMENTS

| | | | |
|---|---|---|---|
| 4,658,085 | 4/1987 | Beversdorf et al. | 800/255 |
| 4,767,888 | 8/1988 | Ayotte et al. | 800/255 |
| 4,943,674 | 7/1990 | Houck et al. | 435/172.3 |
| 4,962,028 | 10/1990 | Bedbrook et al. | 435/172.3 |
| 5,001,060 | 3/1991 | Peacock et al. | 435/172.3 |
| 5,034,322 | 7/1991 | Rogers et al. | 435/172.3 |
| 5,073,675 | 12/1991 | Jones et al. | 800/205 |
| 5,073,676 | 12/1991 | Bridges et al. | 800/205 |

FOREIGN PATENT DOCUMENTS

| | | | |
|---|---|---|---|
| 0255378 | 2/1988 | European Pat. Off. | 536/27 |
| WO91/16421 | 10/1991 | WIPO . | |

OTHER PUBLICATIONS

Radke, et al., "Transformation of *Brassica napus* L. Using *Agrobacterium tumefaciens*: Developmentally Regulated Expression of a Reintroduced Napin Gene," *Theor. Appl. Genet.* (1988) 75:685–694.

Colot, et al., "Identification of DNA Sequences Required For Seed–Specific Activity of a Wheat Storage Protein Gene Promoter in Tobacco," *J. Cell Biochem. Suppl.*, (1987) 11B, vol. 51.

Battey, et al., "Genetic Engineering For Plant Oils: Potential And Limitations," *Tibtech* (1989) 7:122–125.

Goldberg, et al., "Regulation of Gene Expression During Plant Embryogenesis," *Cell* (1989) 56:149–160.

Crouch et al., "Storage Protein mRNA Levels can be Regulated by Abscisic Acid in *Brassica Embryos*," *Molecular Form and Function of the Plant Genome*, eds. van Vloten-–Doting et al. (1985) pp. 555–566.

Altenbach, et al., "Enhancement of the Methionine Content of Seed Proteins by the Expression of a Chimeric Gene Encoding a Methionine–Rich Protein in Transgenic Plants," *Plant Molecular Biology* (1989) 13:513–522.

Knutzon, et al., "Engineering Stearate Levels In Canola Oil Through The Use Of Antisense Stearoyl–ACP Desaturase Gene Constructs," Proceedings of the 1992 Miami Bio/Technology Winter Symposium.

Voelker, et al., "Engineering Laurate Production In Oilseeds," Proceedings of the 1992 Miami Bio/Technology Winter Symposium, p. 102.

Benfey et al., "Regulated Genes in Transgenic Plants," *Science* (1989) 244:174–181.

Matzke, et al., "Deletion analysis of a zein gene promoter in transgenic tobacco plants," *Plant Molecular Bio.* (1990) 14:323–332.

Chen et al (Nov. 1986) Proc. Natl. Acad. Sci. USA 83: 8560–8564.

Knauf (Feb. 1987) Tibtech 5: 40–46.

Crouch et al (1983) Journal of Molecular and Applied Genetics 2: 273–283.

Murphy (1989) Biochemical Society Transactions 17: 685–686.

*Primary Examiner*—Che S. Chereskin
*Attorney, Agent, or Firm*—Donna E. Scherer

[57] ABSTRACT

Novel DNA constructs which may be used as molecular probes or inserted into a plant host are provided. These constructs comprise a sequence obtainable from the Bce4 gene that is capable of directing transcription in seed tissue at least as early as 11 days after anthesis until approximately 30–35 days after anthesis, joined to a nucleic acid sequence of interest, and a transcription termination region. Thus, transcription of a message encoded by a nucleic acid sequence under the control of the Bce4 regulatory region will occur at a specific time of seed development. In this manner, production of exogenous products, as well as modulation of endogenous products, may be achieved.

23 Claims, 11 Drawing Sheets

```
  1 ACCTCAAATCCCAATCTCACAAATACTTCAATAAAAAGACCAAAAAAAATTAAAGCAAAGAAAAGCCTT           69

70 CTTGTGCACAAAAAAAAGAAGAGCCCTTCTAGGTTTTCACGACATGAAGTTCACTACTCTAATGGTCATC          138
                                           METLysPheThrThrLeuMETValIle

139 ACATTGGTGATAATCGCCATCTCGTCCTCCAATTAGAGCAACCACGGTTGAAAGTTTCGGAGAA               207
    ThrLeuValIleIleAlaIleSerSerProValProIleArgAlaThrThrValGluSerPheGlyGlu

208 GTGGCACAATCGTGTGTTGTGACAGAACTCGCCCCATGCTTACCAGCAATGACCACGGCAGGAGACCCG          276
    ValAlaGlnSerCysValValThrGluLeuAlaProCysLeuProAlaMETThrThrAlaGlyAspPro

277 ACTACAGAATGCTGCGACAAACTGGTAGAGCAGAAACCATGTCTTTGTGGTTATATTCGAAACCCAGCC          345
    ThrThrGluCysCysAspLysLeuValGluGlnLysProCysLeuCysGlyTyrIleArgAsnProAla

346 TATAGTATGTATGTTACTTCTCCAAACGGTCGCAAAGTCTTAGATTTTTGTAAGGTTCCTTTTCCTAGT          414
    TyrSerMETTyrValThrSerProAsnGlyArgLysValLeuAspPheCysLysValProPheProSer

415 TGTTAAATCTCTCAAGACATTGCTAAGAAAAATATTATTAAAAATAAAGAATCAAACTAGATCTGATG          483
    Cys .                                                      |
                                                              BglII

484 TAACAATGAATCATCATGTTTATGGTTGAAGCTTTATATGCTGAAGTGTTTGATTTTAT                    540
                                  |
                              HindIII
```

FIGURE 1

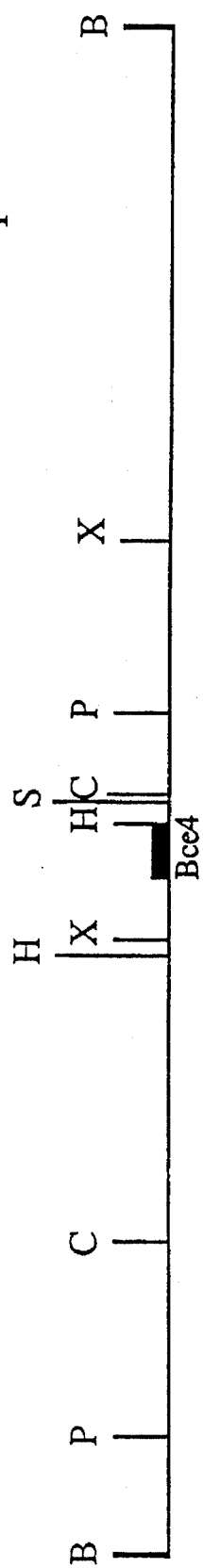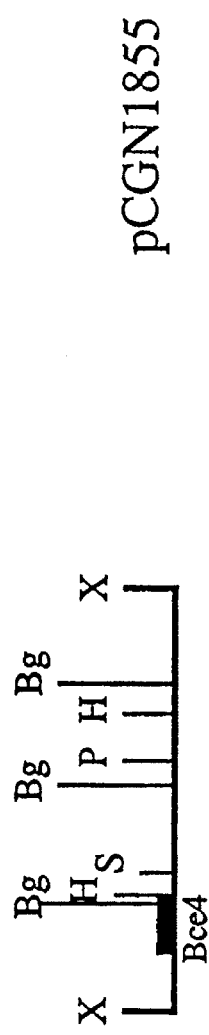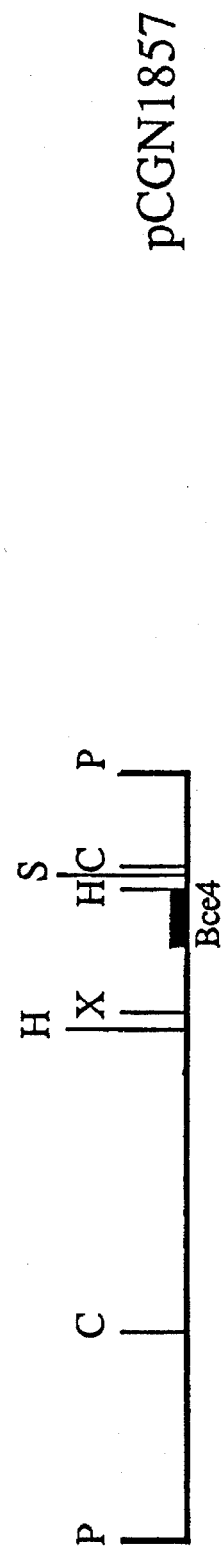
FIGURE 2

```
  1  ATGATTACCTGAAAATAAGTATAATTGTATTGAAATTTATAAAGTGACATTTTTGTGTAACAAATATT    69
 70  TTGTGTAACAAGAATTAAAAAAAAAACAGAAATACTCAGCTTTTTTAATATAAAAAAATTAATTG     138
139  AGTTAGAAAATTGTTGTACCAATAACAAAGATTTATATGGAATTATAAATCAACACCAATAACAC     207
208  AAGACTTTTTAAAAATTTAAGAATAATATAAGCAATAACAATAGAATCTTCAAATCTTCAAATCCTTA  276
277  AAAATCAATCTCCCACTATTAATCCCCCTTAGTTTTTAGTTGGTAATGGCAACGTTTGTTGACTACCGTA 345
346  TTGTAACTTTTGTCAAATTGTCATAAATACGTGTCAAACTCTGGTAAAAAATTAGTCTGCTACATCTGT 414
415  CTTTTATTTATAAAACACAGCTGTTAATCAGAATTTGGTTTATTAAATCAACAACCTGCACGAAACTTG 483
484  TGTGAGCATATTTGTCTGTTTCTGGTTCATGACCTTCTTCCGCATGATGGCCAAGTGTAATGGCCACT   552
                                                                    BglII
                                                                     |
553  TGCAAGAGCGTTCTTCAACGAGATAAGTCGAACAAATATTGTCCGTTACGACCACATATAANATCTC    621
                                                                   616
622  CCCATCTCTATATATAATACCAGCATTCACCATCATGAATACCTCAAATCCCAATCTCACAAATACTTC 690
691  AATAAAAAGACCAAAACAAATTAAAGCAAAGAAAAGCCTTCTTGTGCACAAAAAAGAAGCCTTCT     759
760  AGGTTTTCACGACATGAAGTTCACTACTCTAATGGTCATCACATTGGTGATAATGCCATCTCGTCTCC  828
                METLysPheThrThrLeuMETValIleThrLeuMETValIleAlaIleSerSerPr
```

FIG. 3a

```
829  TGTTCCAATTAGAGCAACCACGGTTGAAAGTTTCGGAGAAGTGGCACAATGTGTTGTGACAGAACT  897
     oValProIleArgAlaThrThrValGluSerPheGlyGluValAlaGlnSerCysValValThrGluLe

898  CGCCCCATGCTTACCAGCAATGACAATGACCCGACTACAGAATGCTGGCACAAACTGGTAGA  966
     uAlaProCysLeuProAlaMETThrThrAlaGlyAspProThrThrGluCysCysAspLysLeuValGl

967  GCAGAAACCATGTCTTTGTGGTTATATTCGAAACCCTAGTAGTATGTTACTTCTCCAAACGG  1035
     uGlnLysProCysLeuCysGlyTyrIleArgAsnProAlaTyrSerMETTyrValThrSerProAsnGl

1036 TCGCAAAGTCTTAGATTTTTGTAAGGTTCCTTTCCTAGTTGTTAAATCTCTCAAGACATTGCTAAGAA  1104
     yArgLysValLeuAspPheCysLysValProPheProSerCys .

Bg1II            HindII
1105 AAATATTATTAAAAATAAAAGAATCAAACTAGATCTGATGTAACAATGAATCATCATGTTATGGTTGAA  1173
                                        1136                                    1173

1174 GCTTATATAGCTGAAGTGTTTTGATTTTATATATGTGTGTGTGTCCTGCTCAATTTTGAAACAC  1242

1243 ACACGTTTCTCCCTGATTTGGATTTAAATTATATTTGAGTTAAAAAAAAGATGGAATGCTATT  1311

EcoRV
1312 TATACAAGTTGATGAAAAGTGGAAGTACAATTTAGATATCTCCWWCACTTAAAGAATGAAACAATAAT  1380
                                                        1350
```

FIG. 3b

```
                                                                         SalI
1381  AGACTTCGAAACAAATGAAAAATACATAAATTGTCGACAATCAACGTCGATCGACGAGTTTATTATTAA  1449
                  1414
1450  AAATTTGTGTGAAGGACTAGCAGTTCAACCAAATGATATTGAACATATACATCAACAAATATGATAATC  1518
1519  ATAAAAGAGAGAATGGGGGGGGTGTCGTTTACCAGAAACCTCTTTTTCTCAGCTCGCTAAACCCTA     1587
1588  CCACTAGAGACCTAGCTCTCGACCGTCGGCTCATCGGTGCCGGAGGTGTAACCTTTCTTTCCCATGACCC  1656
1657  GAAACCCTCTCTTTCCCAACTCACGAAACCCTAGCTCCGACCATCGGCTCATCGG                1725
                                                                         ClaI
1726  TGCCGAAGGTGTAACCTTTCNCTCCCATCATAGTTTCTCGTAAATGAAAGCTAATTGGGCAATGATTT   1794
                                              1789
1795  TTTAATGTTTAAACCATGCCAAGCCATTCTTATAGGACAATTGTCAATAATAGCATCTTTGAGTTTT    1863
1864  GTCTCAAAAGTGACACTAGAAGAAAAAGTCACAAAATGACATTCATTAAAAGTAAATATCCCTAA      1932
1933  TACCTTTGGTTTAAATTAAATAAGTAAACAAAAATAAGAATAAAAAACAAATAAAAATAAAAAATGA    2001
2002  AAAAAAGAAATTTTTTTATAGTTTCAGATTATATGTTTCAGATTCGAAATTTTTAAA             2060
```

FIG. 3c

```
  1 ATGATTACCTGAAAATAAGTATAATTGTATTGAAATTATAAAGTGACATTTTTGTGTAACAAATATT             69
 70 TTGTGTAACAAGAATTAAAAAAAAAACAGAAAATACTCAGCTTTTTAATAATAAAAAAATTAATTG            138
139 AGTTAGAAAATTGTTGTACCAATAACAAAGATTTATATGGAATTATAAATCAACACCAATAACAC            207
208 AAGACTTTTTAAAAATTAAGAATAATAAGCAATAACAATAGAATCTTCAAATTCTTCAAATCCTTA           276
277 AAAATCAATCTCCCACTATTAATCCCCCTTAGTTTTAGTTGGTAATGGCAACGTTTGTTGACTACCGTA         345
346 TTGTAACTTTGTCAAATTGTCATAAATACGTGTCAAACTCTGGTAAAAAATTAGTCTGCTACATCTGT          414
415 CTTTTATTTATAAAACACAGCTGTTAATCAGAATTTGGTTTATTAAATCAACAACCTGCACGAAACTTG         483
484 TGTGAGCATATTTGTCTGTTTCTGGTTCATGACCTTCTTCCCGCATGATGGCCAAGTGTAATGGCCACT         552
                                                                  BglII
553 TGCAAGAGCGTTCTTCAACGAGATAAGTCGAACAAATATTGTCCGTTACGACCACATATAANATCTC          621
622 CCCATCTCTATATATAATACCAGCATTCACCATCATGAATACCTCAAATCCCAATCTCCACAAATACTTC       690
691 AATAAAAAGACCAAAAAATTAAAGCAAAGAAAAATTAAAGGAAGAAAATTAAAGGAGCCTTCT              759
760 AGGTTTTCACGACCCTCGAGGATCCATGAAGTTCACTACTCTAATGGTCATCATCATTGGTGATAATCGCC      828
              XhoI BamHI      METLysPheThrThrLeuMETValIleThrLeuValIleIleAla
829 ATCTCGTCTCCTGTTCCAATTAGAGCAACCGGTTGAAAGTTTCGGAGAAGTGGCACAATCGTGTGTT           897
    IleSerSerProValProIleArgAlaThrThrValGluSerPheGlyGluValAlaGlnSerCysVal
```

FIGURE 4A

898  GTGACAGAACTCGCCCCATGCTTACCAGCAATGACCACGGCAGGAGACCCGACTACAGAATGCTGCGAC  966
     ValThrGluLeuAlaProCysLeuProAlaMETThrThrAlaGlyAspProThrThrGluCysCysAsp

967  AAACTGGTAGAGCAGAAACCATGTCTTTGTGGTTATATTCGAAACCAGCCTATAGTATGTATGTTACT  1035
     LysLeuValGluGlnLysProCysLeuCysGlyTyrIleArgAsnProAlaTyrSerMETTyrValThr
                                                                    BamHI  SmaI

1036 TCTCCAAACGGTCGCAAAGTCTTAGATTTTTGTAAGGTTCCTTTTCCTAGTTGTTAAGGATCCCGGGAT  1104
     SerProAsnGlyArgLysValLeuAspPheCysLysValProPheProSerCys
                                                         BglII

1105 CTCTCAAGACATTGCTAAGAGAAAAATATTAAAAAATAAAGAATCAAACTAGATCTGATGTAACAATG  1173
                                                        HindIII

1174 AATCATCATGTTATGGTTGAAGCTTATATAGCTGAAGTGTTTGATTTTATATATGTGTGTGTGTGTGT  1242

1243 CCTGCTCAATTTTGAAACACACGTTTCTCCCTGATTTGGATTTAAATTATATTTGAGTTAAAAAAAA  1311
                                                         EcoRV

1312 AGAAAAAGATGGAATGCTATTTTATACAAGTTGATGAAAAAGTGGAAGTACAATTAGATATCTCCWWCA  1380
                                                                  SalI

1381 CTTAAAGAATGAAACAATATAGACTTCGAAACAAATGAAAAATACATAAATTGTCGACAATCAACGTC  1449

1450 GATCGACGAGTTTATTATTAAAAATTTGTGTGAAGGACTAGCAGTTCAACCAAATGATATTGAACATAT  1518

1519 ACATCAACAAATATGATAATCATAAAGAGAATGGGGGGGGTGTCGTTTACCAGAAACCTCTTTT  1587

FIGURE 4B

1588 TCTCAGCTCGCTAAAACCCTACCACTAGAGACCTAGCTCTGACCGTCGGCTCATCGGTGCCGGAGGTGT 1656
1657 AACCTTTCTTCCCATGACCCGAAACCTCTCTTCCCAACTCACGAAACCCTACAATCAAAAACCTAG 1725
1726 CTCCGACCATCGGCTCATCGGTGCCGAAGGTGTAACCTTTCNCTCCCATCATAGTTTCTCGTAAATGAA 1794
1795 AGCTAATTGGGCAATCGATTTTTAATGTTAAACCATGCCAAGCCATTCTTATAGACAATTGTCAA 1863
1864 TAATAGCATCTTTTGAGTTTTGTCTCAAAAGTGACACTAGAAGAAAAAGTCACAAAATGACATTCAT 1932
1933 TAAAAAGTAAAAATATCCCTAATACCTTTGGTTTAAATTAAATAAGTAAACAAAAATAAATAAAACAAA 2001
2002 TAAAATAAAAATAAAAATGAAAAAAGAAATTTTTTATAGTTTCAGATTATATGTTTCAGATTCGA 2070
2071 AATTTTTTAAA 2081

FIGURE 4C

```
        SalI
        AccI
        ||
103 GTCGACGAAGATGATGCCACAAATCCAGCCGGCCCATTTAGGATTCCAAAA  153
        104
        105

154 TGTAGGAAGGAGTTTCAGCAAGCACAACACCTGAAAGCTTGCCAACAATGG  204

205 CTCCACAAGCAGGCAATGCAGTCCGGTAGTGGTCCAAGCTGGACCCTCGAT  255

HaeIII
                                              ‾‾‾
256 GGTGAGTTTGATTTTGAAGACGACGTGGAGAACCAACAACAGGGCCCGCAG  306
                                                   300

SacI
                                   ‾‾‾
307 CAGAGGCCACCGCTGCTCCAGCAGTGCTGCAACGAGCTCCACCAGGAAGAG  357
       HaeIII                             343
       ‾‾‾
       313

358 CCACTTTGCGTTTGCCCAACCTTGAAAGGAGCATCCAAAGCCGTTAAACAA  408

409 CAGATTCGACAACAACAGGGACAACAAATGCAGGGACAGCAGATGCAGCAA  459

AluI
                                   ‾‾‾
460 GTGATTAGCCGTATCTACCAGACCGCTACGCCACTTACCTAGAGCTTGCAAC  510
                                                  503
                                                  503
```

FIGURE 6A

```
                                              HaeIII
                                               ApaI  561
                                                 |
511 ATCAGGCAAGTTAGCATTTGCCCCTTCCAGAAGACCATGCCTGGGCCCGGC
                                                    561

XhoI
                      ||
562 TTCTACTAGATTCCAAACGAATATCCTCGAG 592
                                588
```

SEQUENCES PREFERENTIALLY EXPRESSED IN EARLY SEED DEVELOPMENT AND METHODS RELATED THERETO

This is a continuation of application Ser. No. 07/494,722, filed Mar. 16, 1990, now abandoned.

TECHNICAL FIELD

This invention relates to novel in-vitro constructed DNA expression cassettes capable of directing seed-tissue transcription. The invention is exemplified by a promoter useful in seed-tissue transcription in a plant of the genus *Brassica*.

BACKGROUND

The ability to control gene expression at a specific stage of plant growth, or in a specific plant tissue is an ability frequently desired in genetic engineering. To achieve this, nucleic acid sequences are required that will initiate transcription in the desired tissue at the desired stage in the plant growing cycle. One application of this interest is the ability to modify the phenotype of seed tissue, e.g., modifying the protein composition, oil composition, nutritional value, and the like.

In order to isolate useful nucleic acid sequences, a product must be identified that is present in the desired tissue but not present in other tissue. This product may then be used to identify a nucleic acid sequence in the plant genome that contains the flanking regulatory regions. Once the regulatory regions have been identified and isolated, a construct must be engineered so that DNA sequences of interest may be conveniently placed in position to be regulated by these sequences. Finally, the construct must be integrated into a plant genome, and the effect of its presence determined, i.e., ability to initiate transcription and effect phenotype.

Relevant Literature

European Patent Application 0 255 378 (and related European Patent Application 0255 377) describe seed specific transcriptional regulation generally and describe examples of several promoters capable of initiating preferential transcription in various seed tissues.

SUMMARY OF THE INVENTION

Novel DNA constructs which may be used as molecular probes or inserted into a plant host are provided. These constructs comprise a sequence obtainable from the Bce4 gene that is capable of directing transcription in seed tissue at least as early as 11 days after anthesis until approximately 30–35 days after anthesis, joined to a nucleic acid sequence of interest, and a transcription termination region. Thus, transcription of a message encoded by a nucleic acid sequence under the control of the Bce4 regulatory region will occur at a specific time of seed development. In this manner, production of exogenous products, as well as modulation of endogenous products, may be achieved.

Also provided herein are *Agrobacterium*, plant cells, and plants transformed with such constructs.

A deposit of E. coli containing the transcription initiation region on plasmid pCGN1857 has been made at the American Type Culture Collection (Rockville, Md.).

DESCRIPTION OF THE DRAWINGS

FIG. 1 is a DNA sequence of a cDNA clone for Bce4.

FIG. 2 shows partial restriction maps of various genomic subclones of a genomic clone of Bce4. The boxes indicate the location of the Bce4 coding region. B:BamHI, Bg:BglII, C:ClaI, H:HindIII, P:PstI, S:SalI, X:XbaI.

FIG. 3 shows DNA sequence of the Bce4 genomic clone.

FIG. 4 shows DNA sequence of the Bce4 genomic clone after in vitro mutagenesis. Mutagenized sequences are shown in bold type.

FIG. 6 is a DNA sequence of the BE5 cDNA.

DETAILED DESCRIPTION OF THE INVENTION

Figure 5:
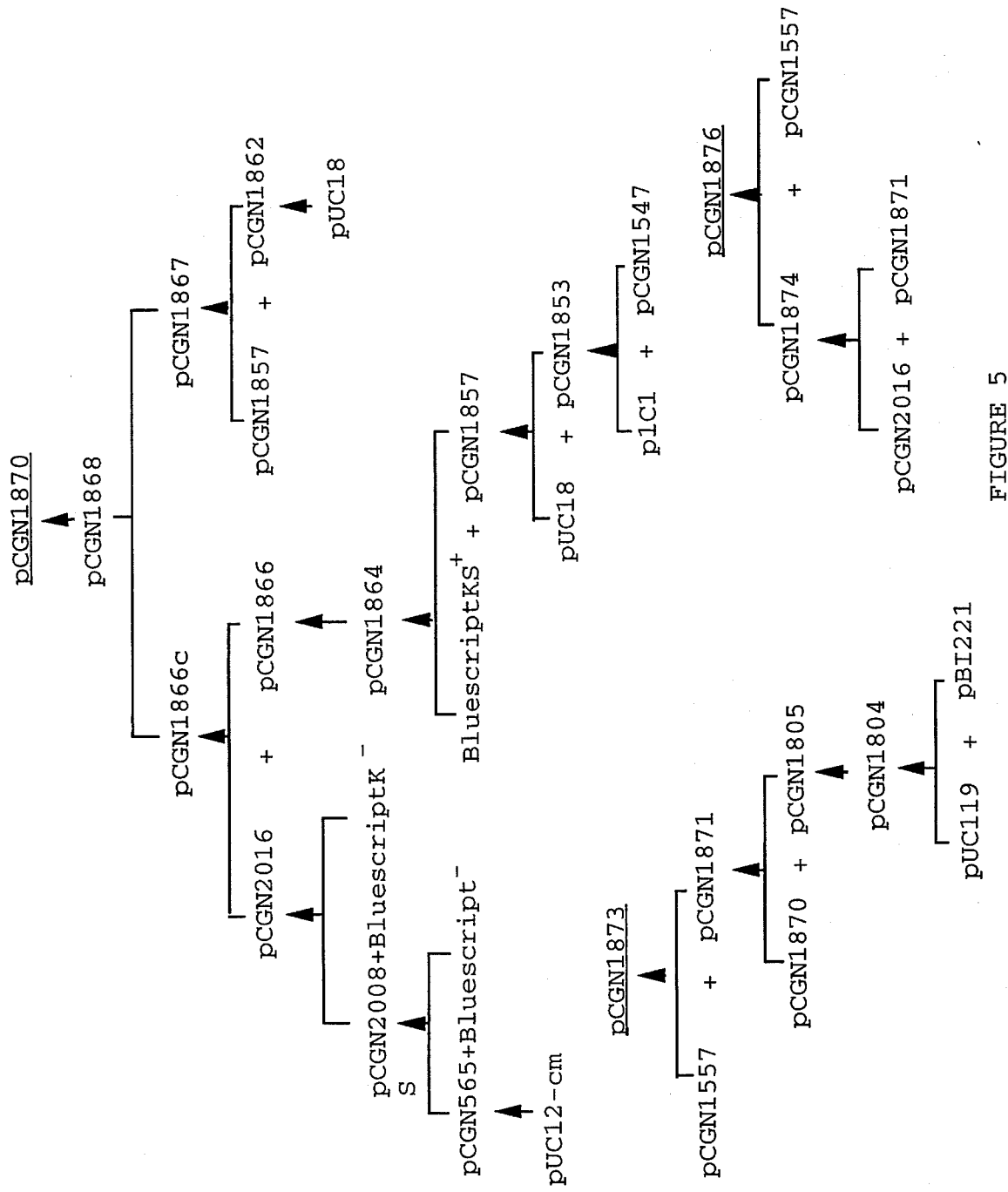
FIG. 5 is a schematic diagram of the construction of the Bce4 expression cassette pCGN1870.

Novel DNA sequences, including plant cells of plant parts and whole plants, constructs employing such sequences, plant cells containing such constructs are provided where the sequences are associated with Bce4.

Bce4 is a plant gene, originally isolated from embryo tissue of Brassica campestris, which displays an expression profile of interest for use in plant biotechnology. Namely, relatively high levels of Bce4 mRNA are observed early in embryo development. Tests indicate that the Bce4 RNA transcripts are present at least 11 days post anthesis, reaching peak levels at approximately 17–19 days post anthesis, and are not detectable at 35 days post anthesis. Bce4 is preferentially expressed in seed embryo tissue. Bce4 mRNA has not been detected in root, seedling or leaf tissue, although some levels have been detected in seed coat tissue.

Although the function of the protein translated from the Bce4 RNA transcripts is not known, because expression of Bce4 coincides with the accumulation of lipids in the plant seed and because Bce4 is preferentially expressed in seed tissue, the regulatory regions associated with the genomic sequence of Bce4 i.e., the non-coding regions found flanking the structural gene, are of interest for genetic engineering applications. Approximately 2 kb of genomic sequence corresponding to Bce4 is given in FIG. 3.

The cDNA sequence encoding Bce4 is also provided herein, FIG. 1. The cDNA sequence, i.e., the coding region for the structural gene, is relatively short: it has an open reading frame of only about 300 bp. Also, it is noted that it does not contain any intron sequences. The short length of the Bce4 coding region allows for ready manipulation of the Bce4 gene for biotechnology applications.

Thus, the regulatory regions associated with the Bce4 gene are desired to effect the transcription or transcription and translation of DNA sequences of interest in plant host cells. When used in a construct, the Bce4 sequence may be endogenous to the target host or exogenous to the target host. In addition, Bce4 regulatory regions associated with termination of transcription are also of interest, especially when used in conjunction with Bce4 upstream transcription initiation sequences.

The region found immediately 5' upstream to the Bce4 coding region provides for the initiation of transcription and translation of the Bce4 structural gene. For some uses the transcription initiation region may be used without translation initiation sequences, such as when the Bce4 transcription initiation region is used to regulate the transcription of a DNA sequence of interest in an anti-sense orientation. The transcription initiation region includes transcriptional control regions such as "TATAA" and "CAAT" box sequences as well as sequences which will regulate the timing and tissue specificity of the transcribed product. The Bce4 translation initiation region, ribosome binding site and other related sequences associated with protein expression of mRNA sequence of the "ATG" start codon, are preferentially used in conjunction with the Bce4 transcription initiation region. The ATG start codon is often provided by the DNA sequence of interest. The use of the Bce4 transcription/translation initiation regions in combination is termed the "Bce4 promoter." Alternatively, in some embodiments, the transcription or translation initiation regions of the Bce4 may be combined with other 5' non-coding regions to create heterologous promoters.

The Bce4 transcription initiation region extends a minimum of 500 bp 5' upstream of the transcriptional start site of the structural gene. More preferably, the transcription initiation region will include at least 1 kb upstream of the transcriptional start site of the structural gene, and most preferably, a Bce4 promoter, i.e., including both the transcription and translational sequences found immediately 5' to the "ATG" start of translation, of at least about 5 or 7 kb is employed.

The regulatory region immediately 3' downstream of the structural gene which controls transcription termination extends at least 100 bp, more preferably 500 bp, more preferred about 700 bp and in a most preferred embodiment at least about 1.5 kb beyond the transcriptional stop codon, "TAA", of the coding region. Sequences employing 1.9 kb of Bce4 3' sequence downstream of the stop codon are also preferred.

Evidence suggests that Bce4 belongs to a single-gene family in *Brassica campestris*, but belongs to a multi-gene family in *Brassica napus*. Among multi-gene families, it is desirable to find the transcription initiation regulatory region which provides a high level of transcription. Thus the transcription initiation regulatory region should provide for at least about 10% of the total Bce4 mRNA, preferably at least about 20%, and more preferably at least about 30%. This can be determined by employing two probes, one probe containing conserved sequence and binds to all Bce4 mRNA, and the other probe being in a polymorphic region of the Bce4 locus which binds uniquely to the Bce4 gene being assayed.

The nucleic acid sequences provided herein may be used to prepare probes used to identify Bce4 genes from plant sources other than *Brassica campestris*. Thus, Bce4 sequence may be isolated from any convenient plant, including other seed-bearing plants, especially other plants of the genus *Brassica*, and other oil seed plants such as sunflower, soybean, safflower, corn, and the like, using various techniques. Particularly, by identifying sequences of the subject plant associated with the Bce4 gene, any conserved sequences may be used as probes for hybridization to DNA or RNA obtained from a number of other plant sources. Usually, the sequence will have at least about 60%, preferably at least about 70%, identity of base pairs, excluding any deletions or mutations that may be present. Thus cDNA libraries may be prepared from the plant source of interest, and the probes used to identify cDNA sequences for Bce4. Conveniently, the target cDNA may be cloned in a plaque-forming virus vector so that hybridizing phage may be plaque-purified. The identified cDNAs may be further subcloned, and the sub-cloned sequence analyzed and used for production of other probes. Probes derived from cDNA sequences may be used to identify genomic sequences in a plant genomic library of the appropriate plant species, and the positive clones analyzed by restriction enzyme digestion. The level of transcription may then be determined in a variety of plant tissues to demonstrate the pattern of transcription in the plant. In this manner, one or more sequences may be identified providing both the coding region, as well as the transcriptional regulatory elements of the gene.

The probes may be considerably shorter than the entire sequence, but should be at least about 10, preferably at least about 15, more preferably at least about 20 nucleotides in length. Longer oligonucleotides are also useful, up to the full length of the Bce4 gene. Both DNA and RNA probes may be used.

In use, the probes are typically labeled in a detectable manner (for example, with $^{32}$P-labeled or biotinylated nucleotides) and are incubated with single-stranded DNA or RNA, which is typically immobilized on a nitrocellulose or nylon filter, from the organism in which a gene is being sought. In this way, nucleic acids which hybridize to the probe may be identified.

Although probes are normally used with a detectable label that allows for easy identification, unlabeled oligonucleotides are also useful, both as precursors of labeled probes and for use in methods that provide for direct detection of DNA or DNA/RNA. Accordingly, the term "oligonucleotide" refers to both labeled and unlabeled forms.

Probes and other discreet nucleic acid sequences are often referred to as "fragments" and may comprise RNA or DNA. An extrachromosomal nucleic acid fragment may exist outside the genome as a single-stranded or double-stranded fragment comprising RNA or DNA and may exist in combination with other sequences as well. Fragments may be found integrated into a viral vector, as part of a DNA construct or a plasmid, i.e., a circularized combination of fragments that contains an origin of replication functional in viruses, bacteria and/or plants.

A DNA construct, as mentioned above, may contain, in the 5' to 3' direction of transcription, a Bce4 transcription initiation region and a DNA sequence of interest which is different from the wild-type Bce4 structural gene sequence. A transcription termination region is optionally present in the DNA construct depending upon the intended use and, if present, may be provided within the DNA sequence of interest, or from a heterologous DNA transcription termination region following the DNA sequence of interest in the 5' to 3' direction of transcription. Preferably, the transcription termination region will be obtainable from the Bce4 gene. The Bce4 transcription initiation region may preferably be found in a Bce4 promoter. When the DNA sequence is under the regulatory control of transcription and translation initiation and transcription termination control regions, the DNA construct is considered an "expression cassette."

The DNA sequence of interest may comprise one of many structural genes. For example, genes may be used to add beneficial agronomic properties to the seed, such as to confer herbicide or pest resistance, alter the ratio and/or composition of nutrients found in the seed, or any other desirable trait.

Regulatory regions derived from the Bce4 gene may be especially useful in applications to modify plant seed fatty acids and/or oils without impact to the rest of the plant. Various alterations are desired, including changing the ratio and/or amounts of the various fatty acids, as to length, saturation, and the like, and in a like fashion, subsequently modify the composition of the plant storage lipids as the fatty acid residues are incorporated into triacylglycerols. These results may be achieved by providing for reduction of expression of one or more endogenous products, particularly enzymes or cofactors, by producing a transcription product which is complementary to the transcription product of a native gene, so as to inhibit the maturation and/or expression of the transcription product, or providing for expression of a structural gene, either endogenous or exogenous, associated with fatty acid synthesis. Expression products associated with fatty acid synthesis include acyl carrier protein (as described in co-pending U.S. Ser. No. 437,764) and stearoyl-ACP desaturase (as described in co-pending "Plant Stearoyl-ACP Desaturase—Compositions and Uses, filed contemporaneously herewith, U.S. Serial No. unassigned), for example.

A DNA construct may be assembled from separate fragments of nucleic acid. These fragments may be obtained from a variety of sources by a variety of techniques. The fragments may be separated from undesirable DNA by the use of restriction enzymes. If useful restriction recognition sites are not conveniently located in the DNA sequence being manipulated, sites may be added using site-directed mutagenesis, polymerase chain reaction, linkers, or the like.

After the desired fragments have been obtained and engineered to have compatible "sticky" or blunt ends, the fragments may be ligated together, forming a plasmid, and transformed into a useful host, such as E. coli for cloning. Plasmid DNA may be isolated from the bacteria and analyzed using, for example, restriction digests, size screening, DNA sequencing, or the like.

The DNA construct may further comprise one or more additional elements such as selectable markers, sequences for translocation of the product, origin(s) of replication, etc. In addition, the DNA construct may contain a second DNA sequence of interest under the regulatory control of a transcription or transcription and translation initiation region different from Bce4. Examples of some additional elements are described in more detail below.

Depending upon the sequence of interest the purpose of the transformation and the particular host, other sequences which may be included in the DNA construct of this invention are sequences which provide for specific functions. In some instances, it may be desirable to provide for translocation of the expression product from the cytoplasm to an organelle or for secretion. In this instance, various transit peptides may be employed for translocating the sequence of interest to an organelle, such as the chloroplast or mitochondrion, or to secrete the protein into the extracellular space or to the cell surface. Various transit peptides have been employed, such as the transit peptide of the small subunit of the *Rubisco* gene, plant EPSP synthase, acyl carrier protein, and the like.

Bce4 regulatory constructs are a valuable additional tool for plant gene engineering in applications calling for two transcription initiation regions. For example, Bce4 constructs may be used to augment other seed-specific 5' upstream regulatory regions, such as obtained from napin and seed-ACP, described in co-pending application Ser. No. 07/147,781, filed Jan. 25, 1988. Transcripts from a napin gene, "napin 1-2'", isolated from *Brassica napus*, may be detected at 18 days post anthesis and peak by 27 days post anthesis. Transcripts from an ACP gene, "Bcg 4-4," isolated from immature embryo's of *B. campestris*, appear in seed embryo tissue but not in seed coat tissue. Thus, use of Bce4 5' upstream regulatory regions in conjunction with other transcript initiation regions which are preferentially expressed in seed may allow one to manipulate and coordinate various combinations of tissue specificity, message levels and timing. Such constructs may also contain a second selectable marker, different from the first selectable marker to aid in determining positive transformation. The second marker may be useful in cloning, providing an alternative method of selection from the first selectable marker.

Transformed plants of this invention include cells which have experienced in vitro addition of DNA as well as progeny carrying the added DNA. By plant cell is meant discrete cells, plant organized or unorganized tissue, plant parts and whole plants. Plant hosts of interest include *Brassica*, especially napus and campestris, sunflower, soybean, safflower, corn, and other seed plants, especially other oilseed plants. Plant cells may be transformed in vitro by co-cultivation with *Agrobacterium*, electroporation, protoplast fusion, microinjection, bombardment with microprojectiles and the like.

Plasmids used in plant transformation which may be transformed into *Agrobacterium tumefaciens* are often called binary vectors. In addition to the transcription regulatory regions, a binary vector may contain the left and more preferably at least a right border of the Ti-plasmid from *Agrobacterium tumefaciens*. The vector may contain origins of replication active in E. coli and *Agrobacterium* so that the plasmid may be replicated in either host. To allow for selection of host cells carrying the binary vector, a selectable marker may be joined to the other components of the vector, i.e., the DNA construct. This marker is preferably an antibiotic resistance marker such as gentamicin, chloramphenicol, kanamycin, ampicillin, and the like.

The genus *Agrobacterium* includes the species *A. tumefaciens*, which causes crown gall disease in plants, and the species *A. rhizogenes*, which causes hairy root disease in plants. The virulence of *A tumefaciens* may be attributed to the Ti (tumor-inducing) plasmid, and the virulence of *A rhizogenes* attributed to the Ri (root-inducing) plasmid. The Ti and Ri plasmids carry regions called T-DNA (transferred DNA) which become integrated into the host plant genome, and from there induce tumor or hairy root formation. Conveniently, these plasmids may be "disarmed" such that the region between the T-DNA regions, which causes tumor induction or hairy root formation, is removed. Subsequently, DNA sequences of interest may be inserted between the T-DNA regions, such constructs commonly being called "expression constructs". This new DNA sequence is then integrated into the plant genome, along with the T-DNA, resulting in a plant containing in its genome this DNA sequence of interest.

Once the cells are transformed, transgenic cells may be selected by means of a marker associated with the expression construct. The expression construct will usually be joined with a marker which will allow for selection of transformed plant cells, as against those cells which are not transformed. The marker will usually provide resistance to an antibiotic, i.e., kanamycin, gentamycin, hygromycin, and the like, which antibiotic is toxic to plant cells at a moderate concentration.

After transformation, the plant cells may be grown in an appropriate medium. In the case of protoplasts the cell wall will be allow to reform under appropriate osmotic conditions. In the case of seeds or embryos, an appropriate germination or callus initiation medium would be employed. For explants, an appropriate regeneration medium would be used.

The callus which results from cells may be introduced into a nutrient medium which provides for the formation of shoots and roots, and the resulting plantlets planted and allowed to grow to seed. During the growth, tissue may be harvested and screened for the presence of expression of the expression construct. After growth, the seed may be collected and replanted. One or more generations may then be grown to establish that the gene is inherited in Mendelian fashion.

The invention now being generally described, it will be more readily understood by reference to the following examples, which are included for purposes of illustration and are not intended to limit the invention.

EXAMPLES

Example I: Isolation of Bce4 cDNA

A. Construction of cDNA Library

Total RNA is isolated from 5 g of *B. campestris* cv. R500 embryos obtained from seeds harvested at days 17–19 post-anthesis. RNA is extracted in 25 mls of 4M guanidine thiocyanate buffer as described by Colbert et al. (PNAS (1983) 80:2248–2252). Polysaccharides are removed from the RNA sample by resuspending the pellet in 6 ml of 1X TE (10 mM Tris/1 mM EDTA pH=8), adding potassium acetate to a concentration of 0.05M, and adding one half volume of ethanol. The sample is placed on ice for 60 minutes and centrifuged for 10 minutes at 3000×g. RNA is precipitated from the supernatant by adding sodium acetate to a concentration of 0.3M followed by the addition of two volumes of ethanol. RNA is recovered from the sample by centrifugation at 12,000×g for 10 minutes and yield calculated by UV spectrophotometry. Two mg of the total RNA is further purified by removing polysaccharides on a 0.25 gm Sigma Cell 50 cellulose column. The RNA is loaded onto the column in 1 ml of loading buffer (20 mM Tris-HCl pH 7.5, 0.5M NaCl, 1 mM EDTA, 0.1% SDS), eluted with loading buffer, and collected in ten 500 μl fractions. Ethanol is added to the ten samples to precipitate the RNA. The samples are centrifuged, and the pellets (in fractions 2–7) resuspended in sterile distilled water, pooled, and again precipitated in ethanol. The sample is centrifuged, and the resulting RNA pellet is enriched for poly(A)+RNA by oligo(dT)-cellulose chromatography (Maniarts et al., *Molecular Cloning*: A Laboratory Manual, (1982) Cold Spring Harbor, N.Y.) and quantitated by UV spectrophotometry.

A *Brassica campestris* day 17–19 post anthesis embryo cDNA library is constructed in plasmid vector pCGN1703 using 5 ug of poly(A)+RNA by a method initially described by Jackson and Larkins (*Plant Physiol.* (1976) 57:5–10) as modified by Goldberg, et al. (*Developmental Biol.* (1981) 53:201–217). The plasmid cloning vector pCGN1703, derived from the commercial cloning vector Bluescribe M13-(Stratagene Cloning Systems; La Jolla, Calif.), is made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with synthetic complementary oligonucleotides having the sequences
5'CGGATCCACTGCAGTCTAGAGGGCCCGGGA 3' and
5'    AATTTCCCGGGCCCTCTAGACTGCAGTG-
GATCCGAGCT 3' . These sequences are inserted to eliminate the EcoRI site, move the BamHI site onto the opposite side of the SstI site found in Bluescribe M13-, and to include new restriction sites PstI, XbaI, ApaI, SmaI. The resulting plasmid pCGN1702, is digested with HindIII and blunt-ended with Klenow enzyme. The linear DNA is partially digested with PvuII and ligated with T4 DNA ligase in dilute solution. A transformant having the lac promoter region deleted is selected (pCGN1703) and is used as the plasmid cloning vector.

The library, which consists of approximately 1.5×10⁵ transformants, is constructed in pCGN1703 by the method of Alexander (*Methods in Enzymology* (1987) 154:41–64). Briefly, poly(A)+RNA is annealed, in excess, to vector DNA that has been T-tailed at the Sac/site using the enzyme terminal deoxynucleotidyl transferase and free dTTP nucleotides. The vector DNA is then used as a primer for the synthesis of the first strand of cDNA by the enzyme reverse transcriptase (BRL; Gaithersburg, Md.), which transcribes complementary DNA from the RNA template. Terminal deoxynucleotidyl transferase and free dGTP nucleotides are then used to add a string of dGTP residues to both 3' ends of the vector/cDNA complex. At this point there are two cDNA molecules per vector. The vector/cDNA is then digested with restriction endonuclease BamHI. This digestion yields two types of DNA fragments. The DNA that will be cloned into E. coli consists of the vector attached to one RNA/cDNA molecule. The other fragment consists solely of RNA/cDNA and cannot be cloned into E. coli as it lacks the genetic information necessary for replication. Following the BamHI digestion, a linker DNA of the following sequence

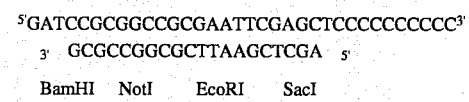

is added to the reaction. The poly(C) residues of this linker anneal to the poly(G) tail of the RNA/cDNA complexes. Reaction conditions are then altered to allow cyclization of the DNA which now contains BamHI restriction sites at both ends. E. coli DNA ligase is added to the reaction to join these ends enzymatically. Finally, the enzymes T4 DNA ligase, RNaseH, and DNA polymerase I (Boehringer-Mannheim, Indianapolis, Ind.) are added to the reaction so that the original RNA template is removed and replaced with DNA. The cDNA (containing plasmid), which now consists of double-stranded cDNA plus vector, is then transformed into competent E. coli DH5α cells (BRL; Gaithersburg, Md.), amplified by plating and scraping colonies, and stored as frozen E. coli cells in 10% DMSO at −80.° C.

DNA is isolated from a portion of the amplified library by scaling up the alkaline lysis technique of Birnboim and Doly (*Nucleic Acids Res.* (1979) 7:1513), and purified by CsCl centrifugation. Library DNA is digested with EcoRI and 0.17 μg is cloned into 1 μg of EcoRI-digested bacteriophage lambda gt10 (Stratagene; La Jolla, Calif.) DNA. The DNA is packaged using Packagene in vitro packaging extracts (Promega; Madison, Wis.) according to manufacturer's specifications. The titer of the phage stock, determined by dilution plating of phage in E. coli C600 cells (Huynh, et al., DNA Cloning. Volume 1. Eds. Gover, D. M. (1985) IRL Press Limited: Oxford, England, pp. 56,110), is 1×10⁶ Pfu per ml. Phage containing the cDNA library inserts are plated, at a concentration of 10³ plaque forming units (pfu) per plate, on two 150 mm diameter round NZY (NZYM medium as defined by Maniatis et al. supra) plates in E. coli C600 cells. Plaques are lifted from the plates onto duplicate nitrocellulose filters as follows. Filters are placed on the plates for two minutes and transferred, plaque side up, to a tray of denaturing solution (1.5M NaCl, 0.5M NaOH) and floated for 1 minute. Filters are then transferred to neutralizing solution (1.5M NaCl, 0.5M Tris-HCl, pH 8.0) for two minutes followed by a three minute wash in 2X SSC (1X =0.15M NaCl, 0.015M sodium citrate, pH 7). Filters are allowed to dry at room temperature and then baked in an 80° C. vacuum oven for two hours.

To screen for seed-specific promoter candidates, the above filters are sequentially probed with radiolabeled DNA prepared by reverse-transcription of *Brassica campestris* leaf mRNA (to eliminate clones expressed in leaves) and reverse-transcription of mRNA from *Brassica campestris* embryos collected at days 17–19 post-anthesis (to identify clones expressed in the embryo). However, since it is assumed that a large proportion of the clones identified as embryo-specific may be clones for the seed storage protein, napin, which are not desired, the filters are also hybridized with a radiolabeled napin cDNA to identify napin clones. All prehybridizations and hybridizations are carried out at 42° C. in 50% formamide, 6X SSC, 5X Denhardt's solution (1X =0.02% polyvinylpyrrolidone/0.02% Ficoll/0.02% bovine serum albumin), and 0.1% denatured salmon sperm DNA. All filters are washed after hybridization in a solution of 0.1X SSC containing 0.1% SDS at 65° C. Autoradiographs are obtained by exposure of the filters to X-ray film at −80° C. with an intensifying screen.

The napin probe is prepared by nick translation according to manufacturer's instructions (Nick Translation System, BRL; Gaithersburg, Md.), using 0.1 μg of an XhoI-SalI DNA fragment from BE5, a napin cDNA clone isolated from a *B. campestris* seed cDNA library FIG. 6. Isolation of BE5 is described in co-pending application U.S. Ser. No. 07/147, 781, filed Jan. 25, 1988, which application is hereby incorporated by reference. The radiolabeled cDNAs from *B. campestris* leaf and embryo mRNA are prepared as follows. 2 μg of mRNA is resuspended in 15 μl of sterile distilled water and a single strand of cDNA is synthesized from the mRNA by addition of 10 μl of BRL 5X M-MLV (Moloney Murine Leukemia Virus) reverse transcriptase buffer (BRL), 40 units of RNasin, ribonuclease inhibitor (Promega; Madison, Wis.), 5 μg of bovine serum albumin, 1.5 μl of a 20 mM solution of nucleotides dATP, dGTP, and dTTP, 1.0 μl of a 0.4 mM solution of dCTP, 1.25 μg of oligo(dT)$_{18}$, 1.9 μg of actinomycin D, 80 uCi of α-$^{32}$P-dCTP, and 500 units of M-MLV reverse transcriptase (BRL) in a final reaction volume of 50 μl. The reaction is run for 60 minutes at 37° C. and then stopped by the addition of 5 μl of 0.25M EDTA. The sample is extracted with phenol:chloroform (50:50), then extracted with chloroform alone. The cDNA is precipitated by addition of ½ volume 7.5M ammonium acetate and 2 volumes ethanol. The sample is placed at −20° C. for 30 minutes and spun in a microcentrifuge to pellet the cDNA. The pellet is resuspended in 100 μl of sterile distilled water, and the amount of radioactive dCTP incorporated is determined by liquid scintillation spectrometry.

Sixteen cDNA clones were identified, by differential screening, as being highly expressed in the seeds and not expressed in leaves. One of these clones, Bce4, was plaque-purified and phage DNA isolated using LambdaSorb phage adsorbent (Promega; Madison, Wis.) following manufacturer's directions. The clone was then returned to plasmid form by digestion with EcoRI, ligation, and transformation into E. coli 71-18 (Yanisch-Perron, et al., Gene (1985) 33:103–119) cells. The clone was further analyzed by DNA sequencing (see below) and Northern and Southern analyses.

The cDNA clone Bce4 was sequenced in the 5' to 3' direction using synthesized oligomers (Applied Biosystems 380A synthesizer, Applied Biosystems; Foster City, Calif.). The oligomers served as primers for sequencing by the dideoxy method (Sanger, et al., PNAS (1977) 74:5463–5467). The sequence is shown in FIG. 1.

B. Northern Analysis

Northern analysis shows that Bce4 is preferentially expressed in seed tissues of *B. campestris*.

RNA is isolated from a number of tissues: *B. campestris* leaves, whole seeds collected on days 15, 19, and 23 post-anthesis, and embryos collected on days 17–19 post-anthesis. Total RNA is isolated by an adaptation of the method of Lagrimini et al. (PNAS (1987) 84:7542–7546). Following homogenization in 2.5 ml/gm grinding buffer, phenol/chloroform extraction and centrifugation as described, RNA is precipitated from the aqueous phase by addition of ⅒ volume 3M sodium acetate and 2 volumes ethanol, followed by freezing at −80° C. for 30 minutes and centrifugation at 13,000×g for 20 minutes. The pellets are washed with 80% ethanol and centrifugation is repeated as above. The pellets are resuspended in water, two volumes of 4M LiCl are added, and the samples placed at −20° C. overnight. Samples are centrifuged as above and the pellets washed with 80% ethanol. Ethanol precipitation is repeated as above. Contaminating polysaccharides are removed by loading the samples on Sigma Cell 50 columns and eluting the RNA as described above. The eluent is ethanol precipitated and the RNA enriched for poly (A)+RNA by oligo (dT) -cellulose column chromatography (Maniatis et al., supra).

Total RNA is isolated from *B. campestris* 3-day old germinating seedlings and roots from the seedlings by extraction in 4M guanidine thiocyanate buffer (Colbert et al., supra). Polysaccharides are removed by precipitation in 50 mM potassium acetate and ½ volume ethanol. The RNA is then precipitated from the supernatants, and the samples enriched for poly(A)+RNA as above.

Total RNA is isolated from day 17 post-anthesis seed coats by an RNA minipreparation technique (Scherer and Knauf, *Plant Mol. Biol.* (1987) 9:127–134) and enriched for poly(A)+RNA as above.

Poly(A)+RNA is quantitated by UV spectrophotometry. Two μg of poly(A)+RNA from *B. campestris* day 17–19 post-anthesis embryos, days 15, 19, and 23 post-anthesis whole seeds, day 17 post-anthesis seed coats, leaves, roots, and seedlings are electrophoresed on formaldehyde/agarose gels (Fourhey et al., Focus (1988) 10(1):5–7) and transferred to a GeneScreen Plus nylon filter (NEN Research Products; Boston, Mass.). The filter is pre-hybridized and hybridized, as described above for the differential screening, at 42° C. overnight. Blots are washed twice, 15 min. each wash, with 1X SSC, 0.1% SDS at 65° C. and once for 30 min. in 0.1X SSC, 0.1% SDS at 65° C., and exposed to X-Ray film.

The results show the presence of an ~700 bp mRNA in the 15, 19 and 23 day post-anthesis whole seed RNA and the 17–19 day post-anthesis embryos. A fainter signal is detected in the seed coat RNA. No hybridization signal is detected in the root, seedling or leaf RNA.

C. Southern Analysis

The number of genes encoding Bce4 in the *B. campestris* genome is determined by Southern blot analysis. Genomic DNA is isolated from young *B. campestris* leaves by the procedure of Dellaporta et al. (Plant Mol. Biol. Rep. (1983) 1:19–21), and purified once by banding in CsCl. Fifty μg of the DNA is digested to completion with the restriction enzymes HindIII, BamHI, SalI, XhoI or BglII. The DNA digests are electrophoresed on a 0.7% agarose gel. The gel is denatured and neutralized, and the DNA transferred to a nitrocellulose membrane as described by Maniatis (supra). Hybridization is carried out with a purified PstI fragment from the Bce4 cDNA clone that is radiolabeled following manufacturer's instructions (Nick Translation System, BRL; Gaithersburg, Md.). Hybridization and wash conditions are as described above for Northern analysis.

The results of hybridization show a single band from each of the above digests suggesting that there is a single gene encoding Bce4 in *B. campestris*. The BamHI digest gave the largest fragment (>15 kb) of all the digests. Similar Southern analysis on B. napus DNA showed hybridization of 3 bands in DNA digests with HindIII, EcoRI, or BglII, indicating there are 3 genes equivalent to Bce4 in the *B. napus* genome.

D. Analysis of Bce4 Localization and Timing

The timing of Bce4 expression during seed development is determined by Northern analysis. Immature seeds of *Brassica campestris* cv. R500 are collected 11, 13, 15, 17, 19, 21, 25, 30, 35, 40, 55, and 60 days post-anthesis. Total RNA is prepared by the method described by Scherer and Knauf (supra). Twenty five micrograms of RNA from each time point are electrophoresed through a formaldehyde-containing 1.5% agarose gel as described by Fourney, Focus (1988) 10(1):5–7) and blotted to nitrocellulose (Thomas, PNAS (1980) 77:5201–5205). The blot is probed with the PstI insert of Bce4 cDNA labeled with $^{32}$P-dCTP by nick translation (Nick Translation Kit, Boehringer Mannhelm; Indianapolis, Ind.). The blot is prehybridized and hybridized in 50% formamide, 10X Denhardt's, 5XSSC, 0.1% SDS, 5 mM EDTA, 100 ug/ml salmon sperm DNA and 10% dextran sulfate (hybridization only) at 42° C. (reagents described in Maniatis, supra). Washes are carried out in 1X SSC and 0.1% SDS for thirty minutes and twice in 0.1X SSC, 0.1% SDS, 15 minutes each wash, at 55° C. The blots are exposed, with an intensifying screen, to X-ray film overnight.

The autoradiograph shows that Bce4 message is present at the earliest time point examined (day 11), peaks at days 17–19 post-anthesis, and is undetectable by 35 days post-anthesis.

Example 2: Isolation of Bce4 Genomic Clone

Southern analysis, described above, indicates that the Bce4 gene is contained on a >15 kb BamHI fragment. Therefore, a directed library is made to large BamHI fragments of genomic DNA, as described below.

Total genomic DNA is isolated from primary leaves of 2–3-week-old *Brassica campestris* cv. R500 seedlings, which are germinated in flats. The leaves are picked and frozen in liquid nitrogen prior to use. Total genomic DNA is isolated by the procedure of Scofield and Crouch (J. Biol. Chem (1987) 262:12202–12208). Two hundred μg of genomic DNA is digested to completion with BamHI and fractionated on sucrose gradients (Maniatis et al., supra). Fractions containing the Bce4 genomic fragment (>15 kb as determined by Southern analysis of aliquots, from fractions, using a nick-translated Bce4 cDNA fragment) are pooled and concentrated by ethanol precipitation.

A *Brassica campestris* genomic library, constructed with BamHI restriction fragments of genomic DNA, is established using the lambda phage vector LambdaGEM-11 (BamHI arms) from Promega (Madison, Wis.) using cloning procedures of Maniatis (supra). The resulting recombinant phage are packaged using GigaPack Gold according to manufacturer's instructions (Stratagene; La Jolla, Calif.), and the library plated on E. coli strain NW2 (Woodcock, et al., *Nucleic Acids Res.* (1989) 17:3469–3478). The titer of the library is approximately $2.6\times10^6$ pfu/ml.

The library is plated by adsorbing the phage to NW2 E. coli cells for 20 minutes at 37° C. and plating on a NZY plate in NZY+10 mM $MgSO_4$ and 0.9% agarose. A total of 150,000 recombinant bacteriophage are screened at a density of 75,000 plaques/9 cm×9 cm plate. The plates are incubated at 37° C. overnight and cooled at 4° C. for 2.5 hours. The phage DNA is transferred, in duplicate, to Genescreen Plus filters (New England Nuclear) by placing precut filters on the plates for approximately 1 minute. The phage DNA is immobilized on the filters by denaturing in 1.5M NaCl, 0.5M NaOH for 1 minute, neutralizing in 1.5M NaCl, 0.5M Tris-HCl, pH 8.0 for 2 minutes, and washing in 2X SSC (Maniatis, supra) for 3 minutes. Filters are air dried until just damp, pre-hybridized and hybridized at 42° C. as described by Maniatis (supra). The filters are probed using a $^{32}$P-labeled PstI fragment (Boehringer Mannheim Nick Translation Kit) isolated from Bce4 cDNA. Washes are carried out at 1 X SSC, 0.1% SDS for thirty minutes and twice in 0.1 X SSC, 0.1% SDS fifteen minutes each wash, at 55° C. The filters are exposed, with an intensifying screen, to X-ray film. A total of six plaques show strong hybridization signals on duplicate filters. Several are plaque purified in E. coli strains NW2 and LE392 (Maniatis, et al., (1982) supra). One clone, identified as PlCl, is further characterized by partial restriction mapping and DNA sequencing. FIG. 2. Phage DNA is isolated by a modified version of the method of Grossberger (*Nucleic Acids Research* (1987) 15(16):6737). Briefly, a plaque is picked and placed in a tube with 0.3 ml of adsorption buffer (10 mM $MgCl_2$ and 10 mM $CaCl_2$) and 0.2 ml LE392 culture in NZY medium. The tube is incubated for 10 minutes at 37° C. and 10 mls ECLB (Maniatis, supra) with 10 mM $MgCl_2$ and 0.1% glucose is added. The tube is shaken overnight at 37° C. When lysis is visible, tube is centrifuged two times at 5–8K RPM for 10 minutes. The supernatant is then centrifuged in a SW41 rotor (Beckman) at 30K RPM for 30 minutes. The pellet is suspended in 200 μl of SM (Maniatis et al., supra) and transferred to a 1.5 ml microfuge tube. 2 ul of 10% SDS is added to tube, mixed well, and the tube is incubated at room temperature for 10 minutes. The mixture is extracted once with phenol and once with chloroform. The DNA is precipitated by addition of 100 ul 7.5M ammonium acetate and 1 ml ethanol.

DNA sequence of the genomic clone PlCl is obtained by double-stranded dideoxy sequencing of pCGN1855. pCGN1855 is constructed by inserting the 5.5 kb XbaI fragment of PlCl, containing the Bce4 gene, into the XbaI site of pUC18 (Norrander et al., Gene, (1983) 26:101–106). DNA sequence is obtained by dideoxy sequencing, as described by Sanger, et al. (PNAS (1977) 74:5463–5467), of a series of nested deletions. Deletions are made in the 5' to 3' direction using ExoIII and SI nucleases, according to the method of Henikoff (Gene (1984) 215:351–359), on KpnI/BamHI-digested pCGN1855 DNA. The sequence obtained begins 662 bp upstream of the start of the cDNA sequence and continues to 856 bp downstream of the end of the cDNA sequence. FIG. 3. PlCl is shown to encode the Bce4 cDNA by its complete homology to the nucleotide sequence of Bce4.

Example 3: Construction of the Bce4 expression cassette

The approximately 20 kb insert of clone PlCl is released by BamHI digestion and inserted into the BamHI site of the binary vector PCGN1547 (see below), producing pCGN1853. The PstI fragment of pCGN1853, containing the Bce4 gene, is inserted into the PstI site of pUC18 (Norrander, et al., (1983) supra), producing pCGN1857. The plasmid pCGN1857 was deposited with the ATCC, Rockville, Md. on Mar. 9, 1990, accession number 68251. The ClaI fragment of pCGN1857, containing the Bce4 gene is ligated into ClaI digested Bluescript KS+ (Stratagene; La Jolla, Calif.), producing pCGN1864. Single stranded DNA is made from pCGN1864 and altered by in vitro mutagenesis using the oligonucleotides

BCE45P:

(5'GAGTAGTGAACTTCATGGATCCTCGAG-GTCTTGAAAACCTAGA3') and

BCE43P:

(5'CAATGTCTTGAGAGATCCCGGGATCCT-TAACAACTAGGAAAAGG3') as described by Adelman et al. (DNA (1983) 2:183–193). The oligonucleotide BSCP2 (5'GTAAGACACGACTTATCGCCACTG3'), complementary to a portion of Bluescript, is included in the reaction to improve the yield of double-stranded DNA molecules. The resulting plasmid, pCGN1866, contains XhoI and BamHI sites (from BCE45P) immediately 5' to the Bce4 start codon and BamHI and SmaI sites (from BCE43P) immediately 3' to the Bce4 stop codon. FIG. 4. The ClaI fragment of pCGN1866, containing the mutagenized sequences, is inserted into the ClaI site of pCGN2016 (described below), producing pCGN1866C. The ClaI fragment of pCGN1866C is used to replace the corresponding wild-type ClaI fragment of pCGN1867 (described below) to produce pCGN1868. Bce4 coding sequences are removed by digestion of pCGN1868 with BamHI and recirculariztion of the plasmid to produce pCGN1870. FIG. 5. The Bce4 expression cassette, pCGN1870, contains 7.4 kb of 5' regulatory sequence and 1.9 kb of 3' regulatory sequence derived from the Bce4 genomic clone separated by the cloning sites, XhoI, BamHI, and SmaI.

pCGN1867

The BamHI and SmaI sites of pUC18 (Norrander et al., (1983) supra) are removed by BamHI-SmaI digestion and recirculariztion of the plasmid, without repair of the ends, to produce pCGN1862. The PstI fragment of pCGN1857, containing the Bce4 gene, is inserted into the PstI site of pCGN1862 to produce pCGN1867.

pCGN2016

The multiple cloning sites of pUC12-Cm (Buckley, K., Ph.D. Thesis, UCSD, Calif. (1985)) are replaced by those of pUC18 to produce pCGN565. The HhaI fragment of pCGN565, containing the chloramphenicol resistance gene is excised, blunted by use of mung bean nuclease, and inserted into the EcoRV site of Bluescript KS- (Stratagene; La Jolla, Calif.) to create pCGN2008. The chloramphenicol resistance gene of pCGN2008 is removed by EcoRI-HindIII digestion. After treatment with Klenow enzyme to blunt the ends, the fragment carrying the chloramphenicol resistance gene is inserted into the DraI site of Bluescript KS-, replacing the ampicillin resistance gene of Bluescript KS-, to produce pCGN2016.

pCGN1547 pCGN1547 (McBride and Summerfelt, *Plant Mol. Biology* (1990) 14(27):269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene of pPhlJI (Hirsch and Beringer, Plasmid (1984) 9:2871–2890), an *Agrobacterium rhizogenes* Ri plasmid origin of replication from pLJbB11 (Jouanin et al., *Mol. Gen. Genet.* (1985) 201:370–374), the mas promoter region and mas 3' region of pTiA6 with the kanamycin resistance gene of Tn5 (Jorgerisen et al., supra), a ColEl origin of replication from pBR322 (Bolivar et al., Gene (1971) 2:95–133), and a lacZ' screenable marker gene from pUC18 (Norrander et al., (1983) supra).

There are three major intermediate constructs used to generate pCGN1547:

pCGN1532 (see below) is made up of the pCGN1547 backbone, the pRi plasmid origin of replication, and the ColEl origin of replication.

pCGN1536 (see below) contains the mas5'-kan-mas3' plant selectable marker region.

pCGN1541b contains the right and left T-DNA borders of the *A. tumefaciens* octopine Ti-plasmid, and the lacZ' region, with multiple cloning sites (to use as a screenable marker in bacteria), from pUC19 (Yanisch-Perron et al., Gene (1985) 33:103–119). The construction of this plasmid is described below.

To construct pCGN1547 from the above plasmids, pCGN1536 is digested with XhoI, and the fragment containing the mas5'-kan-mas3' region is cloned into the XhoI site of pCGN1541b to give the plasmid pCGN1543, which contains T-DNA left border-mas5'-kan-mas3'-lacZ'-T-DNA right border. pCGN1543 is digested with BglII, and the fragment containing the T-DNA left border-mas5'-kan-mas3'-lacZ'-right border region is ligated into BamHI-digested pCGN1532 to give the complete binary vector.

pCGN1532

The 3.5 kb EcoRI-PstI fragment containing the gentamycin resistance gene is removed from pPhlJI (Hirsch and Beringer, Plasmid (1984) 12:139–141) by EcoRI-PstI digestion and cloned into EcoRI-PstI digested pUC9 (Vieira and Messing, Gene (1982) 19:259–268) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., Gene (1977) 2:95–113) to create pBR322Gm. pBR322Gm is digested with DraI and SphI, treated with Klenow enzyme to create blunt ends, and the 2.8 kb fragment cloned into the Ri origin-containing plasmid pLJbB11 (Jouanin et al., *Mol. Gen. Genet.* (1985) 201:370–374) which has been digested with ApaI and made blunt-ended with Klenow enzyme, creating pLHbB11Gm. The extra ColEl origin and the kanamycin resistance gene are deleted from pLHbB11Gm by digestion with BamHI followed by self closure to create pGmB11. The HindIII site of pGmB11 is deleted by HindIII digestion followed by treatment with Klenow enzyme and self closure, creating pGmB11-H. The PstI site of pGmB11-H is deleted by PstI digestion followed by treatment with Klenow enzyme and self-closure, creating pCGN1532.

pCGN1536

The 5.4 kb EcoRI fragment is removed from pVK232 (Knauf and Nester, Plasmid (1982) 8:45), by EcoRI digestion and cloned into EcoRI digested pACYC184 (Chang and Cohen, J. Bacteriol. (1978) 134:1141–1156) to create pCGN14. The 1434 bp ClaI-SphI fragment of pCGN14, containing the mas 5' region (bp20128–21562 according to numbering of Barker et al., *Plant Mo. Biol.* (1983) 2:335–350) is cloned into AccI-SphI digested pUC19 (Yanisch-Perron et al., (1985) supra) to generate pCGN40. A 746 bp EcoRV-NaeI fragment of the mas 5' region is replaced by an XhoI site by digesting pCGN40 with EcoRV and NaeI followed by ligation in the presence of a synthetic XhoI linker DNA to create pCGN1036. The 765 bp SstI-HindIII fragment (bp 18474–19239) of pCGN14, containing the mas 3' region, is cloned into SstI-HindIII digested pUC18 (Norrander et al., (1983) supra) to yield pCGN43. The HindIII site of pCGN43 is replaced with an EcoRI site by digestion with HindIII, blunt ending with Klenow enzyme, and ligation of synthetic EcoRI linker DNA to create pCGN1034. The 767 bp EcoRI fragment of pCGN1034 is cloned into EcoRI-digested pCGN1036 in the orientation that places bp 19239 of the mas 3' region proximal to the mas 5' region to create pCGN1040. pCGN1040 is subjected to partial digestion with SstI, treated with T4 DNA polymerase to create blunt ends, and ligated in the presence of synthetic XhoI linker DNA. A clone is selected in which only the SstI site at the junction of bp 18474 and vector DNA (constructed in pCGN43 and carried into pCGN1040) is replaced by an XhoI site to generate pCGN1047.

pCGN565 (see above) is digested with EcoRI and HindIII, treated with Klenow enzyme to create blunt ends, and ligated in the presence of synthetic XhoI linker DNA to create pCGN1003. This recreates the EcoRI site adjacent to the XhoI linker. pCGN1003 is digested with EcoRI, treated with Klenow enzyme to create blunt ends, and ligated in the presence of synthetic PstI linker DNA to create pCGN1007. The 1.5 kb XhoI fragment of pCGN1047, containing the mas 5' region and the mas 3' region with multiple cloning sites between, is cloned into XhoI digested pCGN1007 to construct pCGN1052. A portion of the multiple cloning site of pCGN1052 is deleted by digestion with XbaI and SstI, treated with Klenow enzyme to make blunt ends, and ligated to generate pCGN1052ΔXS.

The 1 kb EcoRI-SmaI fragment of pCGN783 (pCGN783 is a binary plasmid containing the left and right T-DNA borders of *A. tumefaciens* (Barker et al., *Plant Mol. Biol.* (1983) 2:335–350). The gentamicin resistance gene of pPH1JI (Hirsch et al., Plasmid (1984), 9:2871–2890), the kanamycin resistance gene of Tn5 (Jorgenson et al, *Mol. Gen. Genet.* (1979) 177:65 and Wolff et al., *Nucleic Acids Research* (1985) 13:355–367) and the 3' region from transcript 7 of pTiA6 (Barker et al., supra (1983). The plasmid pCGN783, has been deposited with ATCC (Rockville, Md.), accession number 67868, dated Dec. 23, 1988.), containing the 1ATG-kanamycin resistance gene, is cloned into EcoRI-SmaI digested Bluescript M13-KS (Strategene, Inc., Calif.) to create pBSKm; this plasmid contains an M13 region allowing generation of single stranded DNA. Single stranded DNA is generated according to the supplier's recommendations, and in vitro mutagenesis is performed (Adelman et al., DNA (1983) 2:183–193) using a synthetic oligonucleotide with the sequence 5'GAACTCCAGGACGAGGC3' to alter a PstI site with the kanamycin resistance gene and make it undigestable, creating pCGN1534. pCGN1534 is digested with SmaI and ligated in the presence of synthetic EcoRI linker DNA to generate pCGN1535.

The 1 kb EcoRI fragment of pCGN1535 is cloned into EcoRI digested pCGN1052ΔXS to create the mas5'-kan mas3' plant selectable marker cassette pCGN1536.

pCGN1541b pCGN565RBα2X (see below) is digested with BglII and XhoI, and the 728 bp fragment containing the T-DNA right border piece and the lacZ' gene is ligated with BglII-XhoI digested pCGN65ΔKX-S+K (see below), replacing the BglII-XhoI right border fragment of pCGN65ΔKX-S+K. The resulting plasmid, pCGN65α2X contains both T-DNA borders and the lacZ' gene. The ClaI fragment of pCGN65α2X is replaced with an XhoI site by digesting with ClaI, blunting the ends using the Klenow fragment, and ligating with XhoI linker DNA, resulting in plasmid pCGN65α2XX. pCGN65α2XX is digested with BglII and EcoRV, treated with the Klenow fragment of DNA polymerase I to create blunt ends, and ligated in the presence of BglII linker DNA, resulting in pCGN65α2XX'. pCGN65α2XX' is digested with BglII and ligated with BglII digested pCGN1538 (see below), resulting in pCGN1541a, which contains both plasmid backbones. pCGN1541a is digested with XhoI and religated. Ampicillin resistant, chloramphenicol sensitive clones are chosen, which lack the pACYC184-derived backbone, creating pCGN1541b.

pCGN1538 is generated by digesting pBR322 with EcoRI and PvuII, treating with Klenow to generate blunt ends, and ligating with BglII linkers. pCGN1538 is ampicillin resistant, tetracycline sensitive.

pCGN65ΔKX-S+K pCGN501 is constructed by cloning a 1.85 kb EcoRI-XhoI fragment of pTiA6 (Currier and Nester, J. Bact. (1976) 126:157–165) containing bases 13362–15208 (Barker et al., *Plant Mo. Biol.* (1983) 2:335–350) of the T-DNA (right border), into EcoRI-SalI digested M13mp9 (Vieira and Messing, Gene (1982) 19:259–268). pCGN502 is constructed by cloning a 1.6 kb HindIII-SmaI fragment of pTiA6, containing bases 602–2212 of the T-DNA (left border), into HindIII-SmaI digested M13mp9. pCGN501 and pCGN502 are both digested with EcoRI and HindIII and both T-DNA-containing fragments cloned together into HindIII digested pUC9 (Vieira and Messing, Gene (1982) 19:259–268) to yield pCGN503, containing both T-DNA border fragments. pCGN503 is digested with HindIII and EcoRI and the two resulting HindIII-EcoRI fragments (containing the T-DNA borders) are cloned into EcoRI digested pHC79 (Hohn and Collins, Gene (1980) 11:291–298) to generate pCGN518. The 1.6 kb KpnI-EcoRI fragment from pCGN518, containing the left T-DNA border, is cloned into KpnI-EcoRI digested pCGN565 to generate pCGN580. The BamHI-BglII fragment of pCGN580 is cloned into the BamHI site of pACYC184 (Chang and Cohen, *J. Bacteriol.* (1978) 134:1141–1156) to create pCGN51. The 1.4 kb BamHI-SphI fragment of pCGN60 (see pCGN565α2X description below) containing the T-DNA right border fragment, is cloned into BamHI-SphI digested pCGN51 to create pCGN65, which contains the right and left T-DNA borders.

pCGN65 is digested with KpnI and XbaI, treated with Klenow enzyme to create blunt ends, and ligated in the presence of synthetic BglII linker DNA to create pCGN65ΔKX. pCGN65ΔKX is digested with SalI, treated with Klenow enzyme to create blunt ends, and ligated in the presence of synthetic XhoI linker DNA to create pCGN65ΔKX-S+X.

pCGN565RBα2X pCGN451 (see below) is digested with HpaI and ligated in the presence of synthetic SphI linker DNA to generate pCGN55. The XhoI-SphI fragment of pCGN55 (bp13800–15208, including the right border, of *Agrobacterium tumefaciens* T-DNA; (Barker et al., Gene (1977) 2:95–113) is cloned into SalI-SphI digested pUC19 (Yanisch-Perron et al., (1985) supra) to create pCGN60. The 1.4 kb HindIII-BamHI fragment of pCGN60 is cloned into HindIII-BamHI digested pSP64 (Promega, Inc.) to generate pCGN1039. pCGN1039 is digested with SMAI and NruI (deleting bp14273–15208; (Barker et al., Gene (1977) 2:95–113) and ligated in the presence of synthetic BglII linker DNA, creating pCGN1039ΔNS. The 0.47 kb EcoRI-HindIII fragment of pCGN1039ΔNS is cloned into EcoRI-HindIII digested pCGN565 to create pCGN565RB. The HindIII site of pCGN565RB is replaced with an XhoI site by digesting with HindIII, treating with Klenow enzyme, and ligating in the presence of synthetic XhoI linker DNA to create pCGN565RB-H+X.

pUC18 (Norrander et al., Gene (1983) supra) is digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme in such a orientation that the lacZ' promoter is proximal to the right border fragment. This construct, pCGN565RBα2x is positive for lacZ' expression when plated on an appropriate host and contains bp 13990–14273 of the right border fragment (Barker et al., *Plant Mo. Biol.* (1983) 2:335–350) having deleted the AccI-SphI fragment (bp 13800–13990).

pCGN451 pCGN451 contains an ocs5'-ocs3' cassette, including the T-DNA right border, cloned into a derivative of pUC8 (Vieira and Messing, supra). The modified vector is derived by digesting pUC8 with HincII and ligating in the presence of synthetic linker DNA, creating pCGN416, and then deleting the EcoRI site of pCGN416 by EcoRI digestion followed by treatment with Klenow enzyme and self-ligation to create pCGN426.

The ocs5'-ocs3' cassette is created by a series of steps from DNA derived from the octopine Ti-plasmid pTiA6 (Currier and Nester, supra). To generate the 5' end, which includes the T-DNA right border, an EcoRI fragment of pTiA6 (bp 13362–16202 (the numbering is by Barker, et al., (*Plant Mol. Bio* (1983) 2:335–350) for the closely related Ti plasmid pTi15955)) is removed from pVK232 (Knauf and Nester, Plasmid (1982) 8:45) by EcoRI digestion and cloned into EcoRI digested pACYC184 (Chang and Cohen, supra) to generate pCGN15.

The 2.4 kb BamHI-EcoRI fragment (bp 13774–16202) of pCGN15 is cloned into EcoRI-BamHI digested pBR322 (Bolivar, et al., supra) to yield pCGN429. The 412 bp EcoRI-BamHI fragment (bp 13362–13772) of pCGN15 is cloned into EcoRI-BamHI digested pBR322 to yield pCGN407. The cut-down promoter fragment is obtained by digesting pCGN407 with XmnI (bp 13512), followed by resection with Bal31 exonuclease, ligation of synthetic EcoRI linkers, and digestion with BamHI. Resulting fragments of approximately 130 bp are gel purified and cloned into M13mp9 (Vieira and Messing, supra) and sequenced. A clone, I-4, in which the EcoRI linker has been inserted at bp 1362 between the transcription initiation point and the translation initiation codon is identified by comparison with the sequence of de Greve, et al., (*J. Mol. Appl. Genet.* (1982) 1:499–512). The EcoRI cleavage site is at position 13639, downstream from the mRNA start site. The 141 bp EcoRI-BamHI fragment of I-4, containing the cut-down promoter, is cloned into EcoRI-BamHI digested pBR322 to create pCGN428. The 141 bp EcoRI-BamHI promoter piece from pCGN428, and the 2.5 kb EcoRI-BamHI ocs5 piece from pCGN429are cloned together into EcoRI digested pUC19 (Yanisch-Perron (1985) supra) to generate pCGN442, reconstructing the ocs upstream region with a cut-down promoter section.

To generate the ocs3' end, the HindIII fragment of pLB41 (D. Figurski, UC San Diego) containing the gentamicin resistance gene is cloned into HindIII digested pACYC184 (Chang and Cohen, supra) to create pCGN413b. The 4.7 kb BamHI fragment of pTiA6 (supra), containing the ocs3' region, is cloned into BamHI digested pBR325 (F. Bolivar, Gene (1978) 4:121–136) to create 33c-19. The SmaI site at position 11207 (Barker, supra) of 33c-19 is converted to an XhoI site using a synthetic XhoI linker, generating pCCG401.2. The 3.8 kb BamHI-EcoRI fragment of pCGN401.2 is cloned into BamHI-EcoRI digested pCGN413b to create pCGN419.

The ocs5'-ocs3' cassette is generated by cloning the 2.64 kb EcoRI fragment of pCGN442, containing the 5' region, into EcoRI digested pCGN419 to create pCNG446. The 3.1 kb XhoI fragment of pCGN446, having the ocs5' region (bp 13639–15208) and ocs3' region (bp 11207–12823), is cloned into the XhoI site of pCGN426 to create pCGN451.

Construction of pCGN1557 pCGN1557 (McBride and Summerfelt, *Plant Molecular Biology* (1990) 14(2):269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene of pPhlJI (Hirsch and Beringer, Plasmid (1984) 9:2871–2890), an *Agrobacterium rhizogenes* Ri plasmid origin of replication from pLJbB11 (Jouanin et al., *Mol. Gen. Genet.* (1985) 201:370–374), a 35S promoter-kanR-tml 13' region capable of conferring kanamycin resistance to transformed plants, a ColE1 origin of replication from pBR322 (Bolivar, et al., Gene (1977) 2:95–133), and a lacZ' screenable marker gene from pUC18 (Norrander, et al., (1983) supra).

There are three major intermediate constructs used to generate pCGN1557:

pCGN1532 (See pCGN1547 description) contains the pCGN1557 backbone, the pRi plasmid origin of replication, and the ColE1 origin of replication.

pCGN1546 (see below) contains the CaMV35S5'-kanR-tml 3' plant selectable marker region.

pCGN1541b (see pCGN1547 description) contains the right and left T-DNA borders of the *A. tumefaciens* octopine Ti-plasmid and the lacZ' region from pUC19.

To construct pCGN1557 from the above plasmids, pCGN1546 is digested with XhoI, and the fragment containing the CaMV 35S5'-kan$^R$-tml3' region is cloned into the XhoI site of pCGN1541b to give the plasmid pCGN1553, which contains T-DNA/left border/CaMV 35S5'-kan$^R$-tml 3'/lacZ'/T-DNA left border. pCGN1553 is digested with BglII, and the fragment containing the T-DNA/left border/CaMV35S5'-kan$^R$-tml3'/lacZ'/T-DNA left border region is ligated into BamHI-digested pCGN1532 to give the complete binary vector, pCGN1557.

Construction of pCGN1546

The 35S promoter-tml3' expression cassette, pCGN986, contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMV region VI 3'-end. The CaMV 35S promoter is cloned as an AluI fragment (bp 7144–7734) (Gardner et. al., *Nucl. Acids Res.* (1981) 9:2871–2888) into the HincII site of M13mp7 (Messing, et. al., *Nucl. Acids Res.* (1981) 9:309–321) to create C614. An EcoRI digest of C614 produced the EcoRI fragment from C614 containing the 35S promoter which is cloned into the EcoRI site of pUC8 (Vieira and Messing, Gene (1982) 19:259) to produce pCGN147.

pCGN148a containing a promoter region, selectable marker (KAN with 2 ATG's) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct pCGN528, is made as follows: pCGN525 is made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, J. Bacteriol. (1978) 134:1141–1156). pCGN526 is made by inserting the BamHI fragment 19 of pTiA6 (Thomashow et. al., Cell (1980) 19:729–739), modified with XhoI linkers inserted into the SmaI site, into the BamHI site of pCGN525. pCGN528 is obtained by deleting the small XhoI fragment from pCGN526 by digesting with XhoI and religating.

pCGN149a is made by cloning the BamHI-kanamycin gene fragment from pMB9KanXXI into the BamHI site of pCGN148a. pMB9KanXXI is a pUC4K variant (Vieira and Messing, Gene (1982) 19:259–268) which has the XhoI site missing, but contains a functional kanamycin gene from Tn903 to allow for efficient selection in *Agrobacterium*.

pCGN149a is digested with HindIII and BamHI and ligated to pUC8 digested with HindIII and BamHI to produce pCGN169. This removes the Tn903 kanamycin marker. pCGN565 (see pCGN2016 description) and pCGN169 are both digested with HindIII and PstI and ligated to form pCGN203, a plasmid containing the CaMV 35S promoter and part of the 5'-end of the Tn5 kanamycin gene (up to the PstI site, Jorgenson et. al., (1979), supra). A 3'-regulatory region is added to pCGN203 from pCGN204 (an EcoRI fragment of CaMV (bp 408–6105) containing the region VI 3' cloned into pUC18 (Norrander, et al., Gene (1983) supra) by digestion with HindIII and PstI and ligation. The resulting cassette, pCGN206, is the basis for the construction of pCGN986.

The pTiA6 T-DNA tml3'-sequences are subcloned from the Bam19 T-DNA fragment (Thomashow et al., (1980) supra) as a BamHI-EcoRI fragment (nucleotides 9062 to 12,823, numbering as in Barker et al., *Plant Mol. Biol.* (1982) 2:335–350) and combined with the pACYC184 (Chang and Cohen (1978), supra) origin of replication as an EcoRI-HindIII fragment and a gentamycin resistance marker (from plasmid pLB41), obtained from D. Figurski as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers. The resulting EcoRI-SacI fragment containing the tml 3' regulatory sequences is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI, KpnI and the tml 3' region (nucleotides 11207–9023 of the T-DNA).

The 35S promoter-tml 3' expression cassette, pCGN986 is digested with HindIII. The ends are filled in with Klenow polymerase and XhoI linkers added. The resulting plasmid is called pCGN986X. The BamHI-SacI fragment of pBRX25 (see below) containing the nitrilase gene is inserted into BamHI-SacI digested pCGN986X yielding pBRX66.

Construction of pBRX25 is described in U.S. Pat. No. 4,810,648, which is hereby incorporated by reference. Briefly, the method is as follows: The nucleotide sequence of a 1212-bp PstI-HincII DNA segment encoding the bromoxynil-specific nitrilase contains 65-bp of 5' untranslated nucleotides. To facilitate removal of a portion of these excess nucleotides, plasmid pBRX9 is digested with PstI, and treated with nuclease Bal31. BamHI linkers are added to the resulting ends. BamHI-HincII fragments containing a functional bromoxynil gene are cloned into the BamHI-SmaI sites of pCGN565. The resulting plasmid, pBRX25, contains only 11 bp of 5' untranslated bacterial sequence.

pBRX66 is digested with PstI and EcoRI, blunt ends generated by treatment with Klenow polymerase, and XhoI linkers added. The resulting plasmid pBRX68 now has a tml 3' region that is approximately 1.1 kb. pBRX68 is digested with SalI and SacI, blunt ends generated by treatment with Klenow polymerase and EcoRI linkers added. The resulting plasmid, pCGN986XE is a 35S promoter—tml3' expression cassette lacking the nitrilase gene.

The Tn5 kanamycin resistance gene is then inserted into pCGN986XE. The 1.0 kb EcoRI fragment of pCGN1536 (see pCGN1547 description) is ligated into pCGN986XE digested with EcoRI. A clone with the Tn5 kanamycin resistance gene in the correct orientation for transcription and translation is chosen and called pCGN1537b. The 35S promoter Kan$^R$-tml 3' region is then transferred to a chloramphenical resistant plasmid backbone. pCGN786, (a pUC-CAM based vector with the synthetic oligonucleotide 5' GGAATTCGTCGACAAGATCTCTG-CAGCTCGAGGGATCCAAGCTT3' containing the cloning sites EcoRI, SalI, BglII, PstI, XhoI, BamHI, and HindIII inserted into pCGN566, pCGN566 contains the EcoRI-HindIII linker of pUC18 inserted into the EcoRI-HindIII sites of pUC13-cm (K. Buckley (1985) supra)) is digested with XhoI and the XhoI fragment of pCGN1537b containing the 35S promoter—Kan$^R$-tml3' region is ligated in. The resulting clone is termed pCGN1546.

Example 4: Use of Bce4 cassette to express Gus aene in transgenic plants

Various portions of the Bce4 expression cassette may be used to drive expression of genes in transgenic plants and their expression patterns may be compared. Two examples, derived from pCGN1870 (described in Example 3) are pCGN1873 and pCGN1876, and are described below.

The BamHI-SstI fragment of pBI221 (Jefferson, et al., EMBO (1987) 6:3901–3907), containing the β-glucuronidase (gus) gene is ligated with BamHI-SstI-digested pUC119 (Vieira and Messing, *Methods in Enzymology* (1987) 153:3–4) to produce pCGN1804. pCGN1804 is digested with EcoRI and blunted by treatment with E. coli DNA polymerase I. Commercially available phosphorylated XhoI linkers (P-L Biochemicals; Piscataway, N.J.) are inserted into the blunted EcoRI site to produce pCGN1805. Ligation with the XhoI linkers regenerates an EcoRI site on either side of the XhoI site of pCGN1805. The SalI-XhoI fragment of pCGN1805 containing the gus gene is inserted into the XhoI site of pCGN1870 to produce pCGN1871. The PstI fragment of pCGN1871, containing the gus gene in the Bce4 cassette is inserted into the PstI site of pCGN1557 (described above) to produce pCGN1873. pCGN1873 contains the gus gene under the control of 7.4 kb of Bce4 5' and 1.9 kb of Bce4 3' regulatory sequences.

The ClaI fragment of pCGN1871, containing the gus gene, is inserted into the ClaI site of pCGN2016 to produce pCGN1874. The Asp718-PstI fragment of pCGN1874, containing the gus gene in the Bce4 cassette is inserted between the Asp718 and PstI sites of pCGN1557 to create pCGN1876. pCGN1876 contains the gus gene under the control of 5.1 kb of Bce4 5' and 0.7 kb of Bce4 3' regulatory sequences.

The binary vectors pCGN1873 and pCGN1876 are transformed into *Agrobacterium tumefaciens* strain EHA101 (Hood, et al., J. Bacteriol. (1986) 168:1291–1301) and used to transform *Brassica napus hypocotyls* as described in Example 4.

Example 4: Generation of Transformed Plants

Plant Material and Transformation

Seeds of *Brassica napus* cv. *Westar* are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco) supplemented with pyriodoxine (50 μg/l), nicotinic acid (50 μg/l), glycine (200 μg/l), and 0.6% Phytagar (Gibco) pH 5.8. Seeds are germinated in a Percival chamber at 22° C. in a 16 h photoperiod with cool fluorescent and red light of intensity approximately 65 μ Einsteins per square meter per second ($\mu Em^{-2}s^{-1}$).

Hypocotyls are excised from 5–7 day old seedlings, cut into pieces approximately 4 mm in length, and plated on feeder plates (Horsch et al. 1985). Feeder plates are prepared one day before use by plating 1.0 ml of a tobacco suspension culture onto a petri plate (100×25 mm) containing about 30 ml MS salt base (Carolina Biological) 100 mg/l inositol, 1.3 mg/l thiamine-HCl, 200 mg $KH_2PO_4$ with 3% sucrose, 2,4-D (1.0 mg/l), 0.6% Phytagar, and pH adjusted to 5.8 prior to autoclaving (MS0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of *A. tumefaciens* strain EHA 101 containing a binary plasmid are transferred to 5 ml MG/L broth and grown overnight at 30° C. Hypocotyl explants are immersed in 7–12 ml MG/L broth with bacteria diluted to $1\times10^8$ bacteria/ml and after 10–25 min. are placed onto feeder plates. After 48 h of co-incubation with *Agrobacterium*, the hypocotyl explants are transferred to B5 0/1/0 callus induction medium which contains filter sterilized carbenicillin (500 mg/l, added after autoclaving) and kanamycin sulfate (Boehringer Mannheim) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for NPT II activity.

As seen from the foregoing, a DNA sequence under the regulatory control of the Bce4 5' upstream regulatory region will demonstrate preferentially expression in seed tissue. In accordance with the subject invention, the Bce 4 regulatory regions provide a method to impart useful properties especially to modify the nutritional content of the seed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A DNA construct comprising as operably linked components, in the 5' to 3' direction of transcription, a regulatory region comprising a transcription initiation region from the *B. campestris* Bce4 structural gene shown in FIG. 1 or from a plant gene which binds under stringent hybridization conditions to the Bce4 structural gene sequence shown in FIG. 1, and a DNA sequence of interest which is different from the intact wild-type structural gene sequence associated with said transcription initiation region.

2. The DNA construct of claim 1 wherein said transcription initiation region comprises at least 500 bp immediately upstream of the Bce4 structural gene shown in FIG. 1.

3. The DNA construct of claim 1 wherein said regulatory region further comprises, 3' to said transcription initiation region and 5' to said DNA sequence of interest, the 5' untranslated region of the Bce4 gene shown in FIG. 1.

4. The DNA construct of claim 3 wherein said regulatory region comprises at least 5.1 kb immediately upstream of the Bce4 structural gene shown in FIG. 1.

5. The DNA construct of claim 3 wherein said regulatory region comprises at least 7.4 kb immediately upstream of the Bce4 structural gene shown in FIG. 1.

6. The DNA construct of claim 1 further comprising a transcript termination region functional in a plant cell.

7. The DNA construct of claim 6 wherein said transcript termination region comprises at least 0.7 kb immediately downstream of the Bce4 structural gene shown in FIG. 1.

8. The DNA construct of claim 6 wherein said transcript termination region comprises at least 1.9 kb immediately downstream of the Bce4 structural gene shown in FIG. 1.

9. The DNA construct of claim 1 or 6 wherein said DNA sequence of interest is an antisense DNA sequence.

10. The DNA construct of claim 6 wherein said DNA sequence of interest is a structural gene sequence.

11. The DNA construct of claim 6 wherein said DNA sequence of interest is a DNA sequence which encodes one or more cloning sites.

12. The DNA construct of claim 1 comprising a *B. campestris* Bce4 transcription initiation region.

13. A method of modifying the phenotype of a *Brassica* plant seed comprising the steps of growing a *Brassica* plant having integrated in its genome, or in the genome of a parent thereof, a DNA construct comprising, in the 5' to 3' direction of transcription, a transcription initiation region from the *B. campestris* Bce4 structural gene shown in FIG. 1 or from a plant gene which binds under stringent hybridization conditions to the Bce4 structural gene sequence shown in FIG. 1, and a DNA sequence of interest capable of modifying the phenotype of *Brassica* plant tissue, wherein said DNA sequence of interest is different from the intact wild-type structural gene sequence associated with said transcription initiation region, and whereby said DNA sequence is transcribed in *Brassica* embryo and seed coat tissue.

14. *Brassica* seed produced according to the method of claim 13, wherein said *Brassica* seed has a modified phenotype as the result of transcription of said DNA sequence of interest in embryo and seed coat tissue of said *Brassica* seed.

15. A method of using a Bce4 transcriptional initiation region to provide for transcription of a DNA sequence of interest in a *Brassica* plant seed comprising the steps of growing a *Brassica* plant having integrated in its genome, or in the genome of a parent thereof, a DNA construct comprising, in the 5' to 3' direction of transcription, a transcription initiation region from the

*B. campestris* Bce4 structural gene shown in FIG. 1 or from a plant gene which binds under stringent hybridization conditions to the Bce4 structural gene sequence shown in FIG. 1, and a DNA sequence of interest, and whereby said DNA sequence of interest is transcribed in *Brassica* embryo and seed coat tissue.

16. The method of claim 15 wherein said DNA sequence is antisense DNA sequence.

17. The method of claim 13 or 15 wherein said DNA construct comprises a regulatory region comprising said Bce4 transcription initiation region and a 5' untranslated region from the *B. campestris* Bce4 structural gene shown in FIG. 1 or from a plant gene which binds under stringent hybridization conditions to the Bce4 structural gene sequence shown in FIG. 1.

18. The method of claim 17 wherein said regulatory region comprises at least 5.1 kb immediately upstream of the Bce4 structural gene shown in FIG. 1.

19. The method of claim 17 wherein said regulatory region comprises at least 7.4 kb immediately upstream of the Bce4 structural gene shown in FIG. 1.

20. The DNA construct of claim 3 wherein said regulatory region comprises nucleotides 1–772 of FIG. 3.

21. An oilseed crop plant cell comprising a DNA construct according to claim 1.

22. A *Brassica* plant cell comprising a DNA construct according to claim 1.

23. A plant comprising a plant cell according to claim 21 or 22.

* * * * *